(12) United States Patent
Ayanoor-Vitikkate et al.

(10) Patent No.: US 8,818,527 B2
(45) Date of Patent: Aug. 26, 2014

(54) SYSTEMS AND METHODS FOR MAKING AND USING ENHANCED ELECTRODES FOR ELECTRICAL STIMULATION SYSTEMS

(71) Applicant: Boston Scientific Neuromodulation Corporation, Valencia, CA (US)

(72) Inventors: Vipin Ayanoor-Vitikkate, Valencia, CA (US); Anne Margaret Pianca, Santa Monica, CA (US); Michael S. Colvin, Newbury Park, CA (US); John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/936,953

(22) Filed: Jul. 8, 2013

(65) Prior Publication Data

US 2013/0296956 A1 Nov. 7, 2013

Related U.S. Application Data

(62) Division of application No. 13/220,037, filed on Aug. 29, 2011, now Pat. No. 8,504,171.

(60) Provisional application No. 61/378,773, filed on Aug. 31, 2010.

(51) Int. Cl.
*A61N 1/05* (2006.01)
*A61N 1/36* (2006.01)

(52) U.S. Cl.
CPC .............. *A61N 1/05* (2013.01); *A61N 1/36071* (2013.01); *A61N 1/36067* (2013.01); *A61N 1/36096* (2013.01); *A61N 1/36064* (2013.01)

USPC ........................................................... 607/117

(58) Field of Classification Search
USPC .................................................. 607/115–117
See application file for complete search history.

(56) References Cited

U.S. PATENT DOCUMENTS

| 4,649,937 | A | | 3/1987 | DeHaan et al. |
| 5,271,417 | A | | 12/1993 | Swanson et al. |
| 5,318,572 | A | * | 6/1994 | Helland et al. ................. 607/121 |

(Continued)

OTHER PUBLICATIONS

International Search Report and Written Opinion for International Patent Application No. PCT/US2011/049604 mailed Nov. 14, 2011.

(Continued)

*Primary Examiner* — Rex R Holmes
(74) *Attorney, Agent, or Firm* — Lowe Graham Jones PLLC; Patrick R. Turner

(57) ABSTRACT

A lead assembly for providing electrical stimulation of patient tissue includes at least one elongated lead body, each of the at least one lead bodies having a distal end and a proximal end. A plurality of electrodes are disposed at the distal end of the at least one lead body, each of the electrodes having an outer surface. A plurality of dimples are defined along the outer surface of at least one of the plurality of electrodes, the plurality of dimples configured and arranged to provide a larger surface area for the at least one dimpled electrode than that of a similarly-sized electrode with a flat outer surface. A plurality of terminal are disposed at the proximal end of the at least one lead body. A plurality of conductive wires couple each of the plurality of electrodes to at least one of the plurality of terminals.

20 Claims, 15 Drawing Sheets

(56) References Cited

U.S. PATENT DOCUMENTS

| | | | |
|---|---|---|---|
| 5,330,700 A | 7/1994 | Soukup et al. | |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,218,971 B2 * | 5/2007 | Heil et al. | 607/121 |
| 7,244,150 B1 | 7/2007 | Brase et al. | |
| 7,351,921 B1 | 4/2008 | Haller et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,809,446 B2 | 10/2010 | Meadows | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 2005/0038489 A1 * | 2/2005 | Grill | 607/116 |
| 2007/0150036 A1 | 6/2007 | Anderson | |
| 2007/0265692 A1 | 11/2007 | Koop et al. | |
| 2009/0187222 A1 | 7/2009 | Barker | |
| 2009/0276021 A1 | 11/2009 | Meadows et al. | |
| 2010/0070010 A1 | 3/2010 | Simpson | |
| 2010/0076535 A1 | 3/2010 | Pianca et al. | |
| 2010/0100165 A1 * | 4/2010 | Swanson et al. | 607/117 |
| 2010/0268298 A1 | 10/2010 | Moffitt et al. | |

OTHER PUBLICATIONS

U.S. Appl. No. 12/177,823, filed Jul. 22, 2008.

U.S. Appl. No. 13/220,037 Official Communication mailed Jan. 25, 2013.

* cited by examiner

SYSTEMS AND METHODS FOR MAKING AND USING ENHANCED ELECTRODES FOR ELECTRICAL STIMULATION SYSTEMS

CROSS-REFERENCE TO RELATED APPLICATIONS

This application is a divisional of U.S. patent application Ser. No. 13/220,037 filed Aug. 29, 2011, now U.S. Pat. No. 8,504,171, which claims the benefit under 35 U.S.C. §119(e) of U.S. Provisional Patent Application Ser. No. 61/378,773 filed on Aug. 31, 2010, all of which are incorporated herein by reference.

FIELD

The present invention is directed to the area of implantable electrical stimulation systems and methods of making and using the systems. The present invention is also directed to implantable electrical stimulation leads that include electrodes with enhanced outer surfaces, as well as methods of making and using the electrical stimulation leads, electrodes, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead assembly for providing electrical stimulation of patient tissue includes at least one elongated lead body, each of the at least one lead bodies having a distal end and a proximal end. A plurality of electrodes are disposed at the distal end of the at least one lead body, each of the electrodes having an outer surface. A plurality of dimples are defined along the outer surface of at least one of the plurality of electrodes, the plurality of dimples configured and arranged to provide a larger surface area for the at least one dimpled electrode than that of a similarly-sized electrode with a flat outer surface. A plurality of terminal are disposed at the proximal end of the at least one lead body. A plurality of conductive wires couple each of the plurality of electrodes to at least one of the plurality of terminals.

In another embodiment, a medical lead for providing electrical stimulation of patient tissue includes an elongated lead body having a distal end and a proximal end. A plurality of electrodes are disposed at the distal end of the lead body, each of the plurality of electrodes having a width and an outer surface. At least one of the electrodes defines a plurality of grooves along the outer surface that extend non-linearly along the width of the electrode such that the grooves form a curved line. A plurality of terminals are disposed at the proximal end of the lead body. A plurality of conductive wires couple each of the plurality of electrodes to at least one of the plurality of terminals.

In yet another embodiment, an electrical stimulation lead for providing electrical stimulation of patient tissue includes an elongated lead body having a distal end and a proximal end. A plurality of electrodes are disposed at the distal end of the lead body. Each of the plurality of electrodes has an outer surface. At least some of the electrodes are segmented electrodes that extend around a lateral circumference of the lead body. At least one of the segmented electrodes defines a surface texture defined in the outer surface of the segmented electrode, the surface texture configured and arranged to provide a larger surface area for the at least one dimpled electrode than that of a similarly-sized electrode with a flat outer surface. A plurality of terminals are disposed at the proximal end of the lead body. A plurality of conductive wires couple each of the plurality of electrodes to at least one of the plurality of terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads that include electrodes with enhanced outer surfaces, as well as methods of making and using the electrical stimulation leads, electrodes, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; 8,175,710; 8,224,450; 8,364,278; and U.S. Patent Application Publication No. 2007/0150036, all of which are incorporated by reference.

Figure 1:
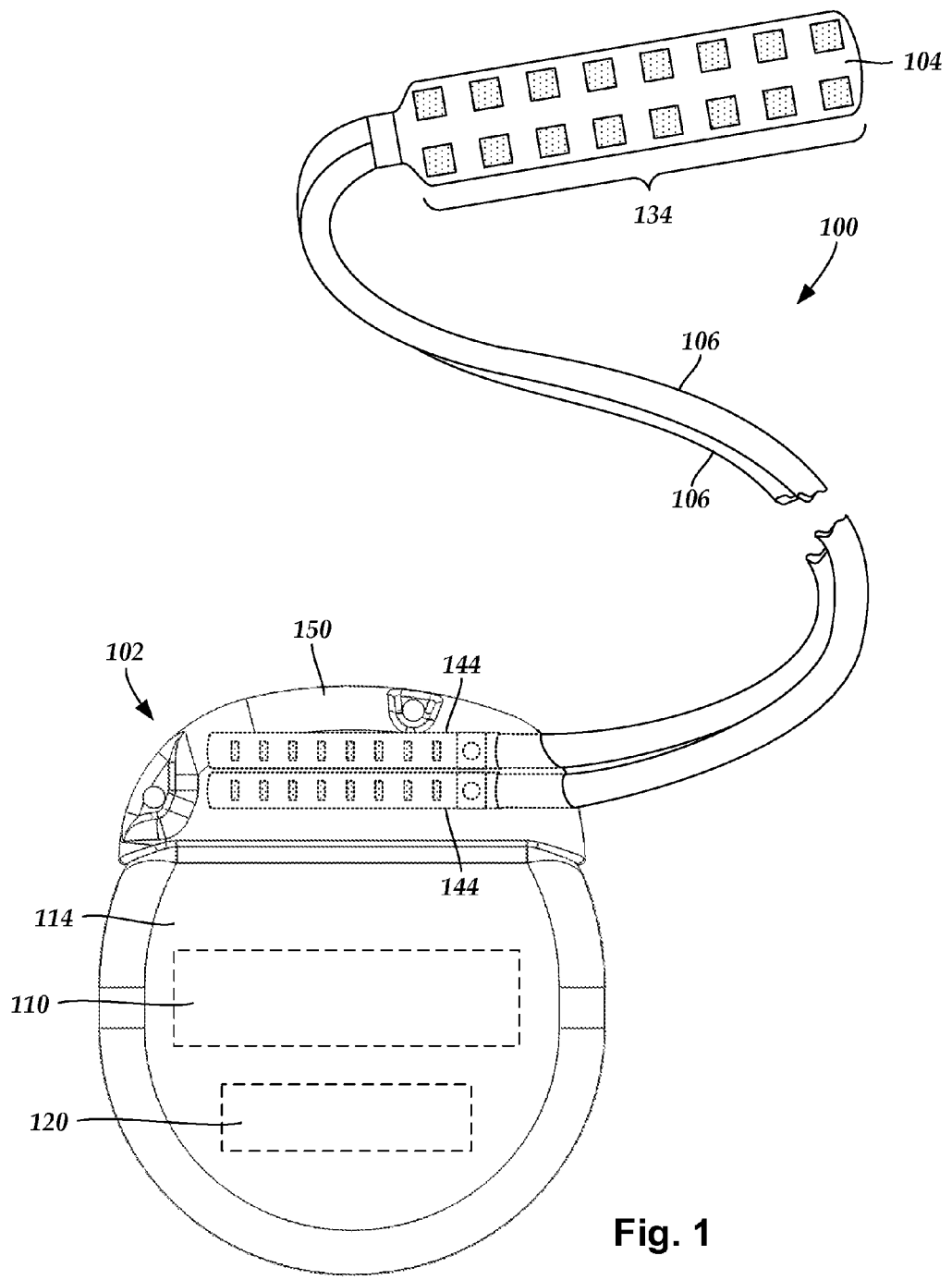
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
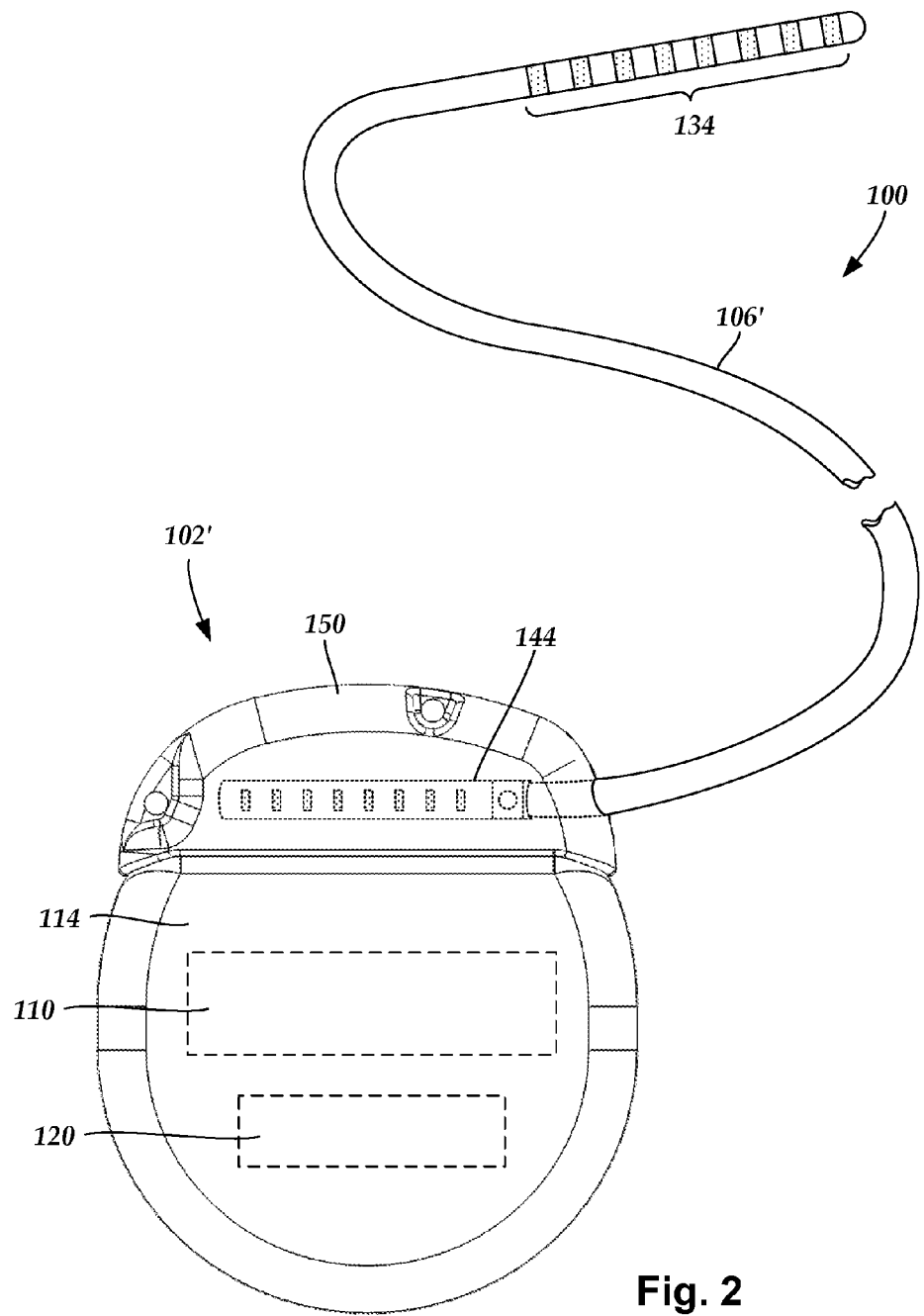
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient.

Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
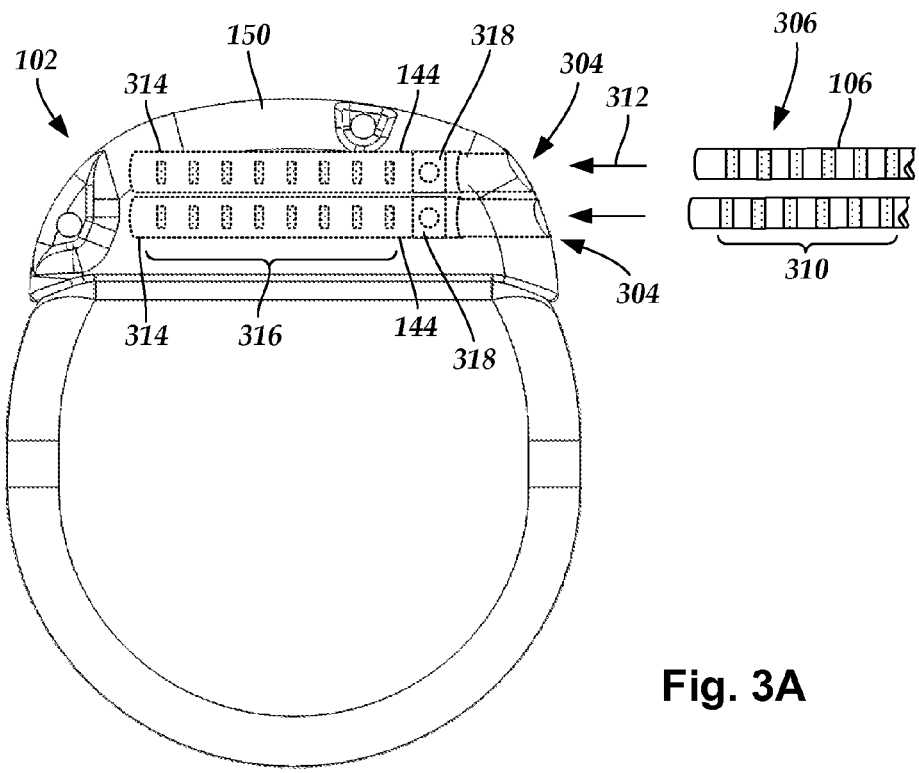
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
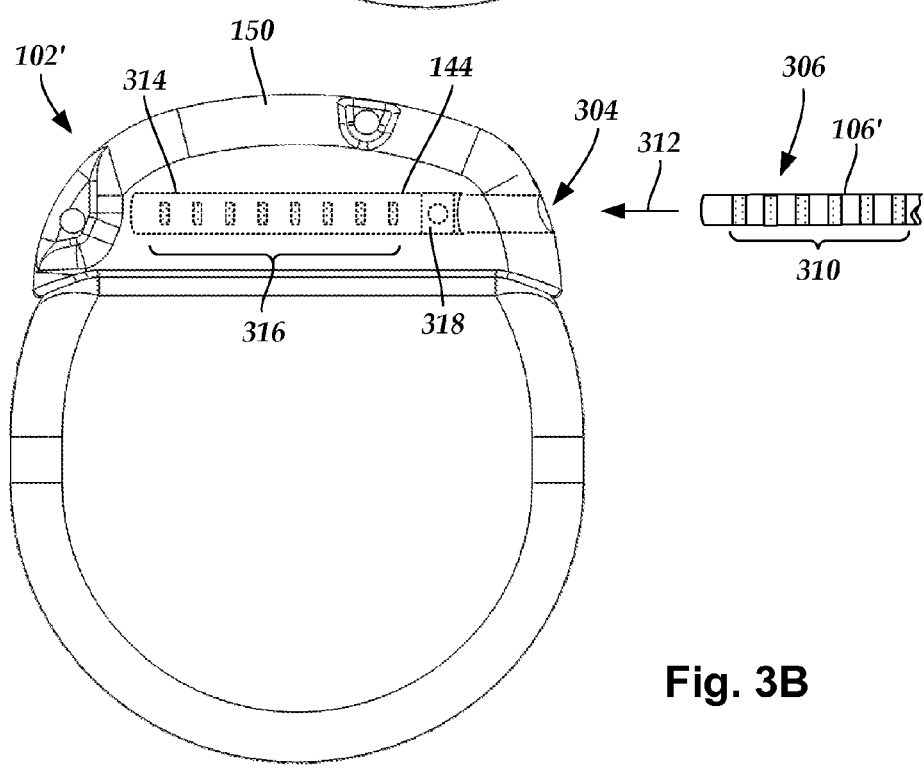
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
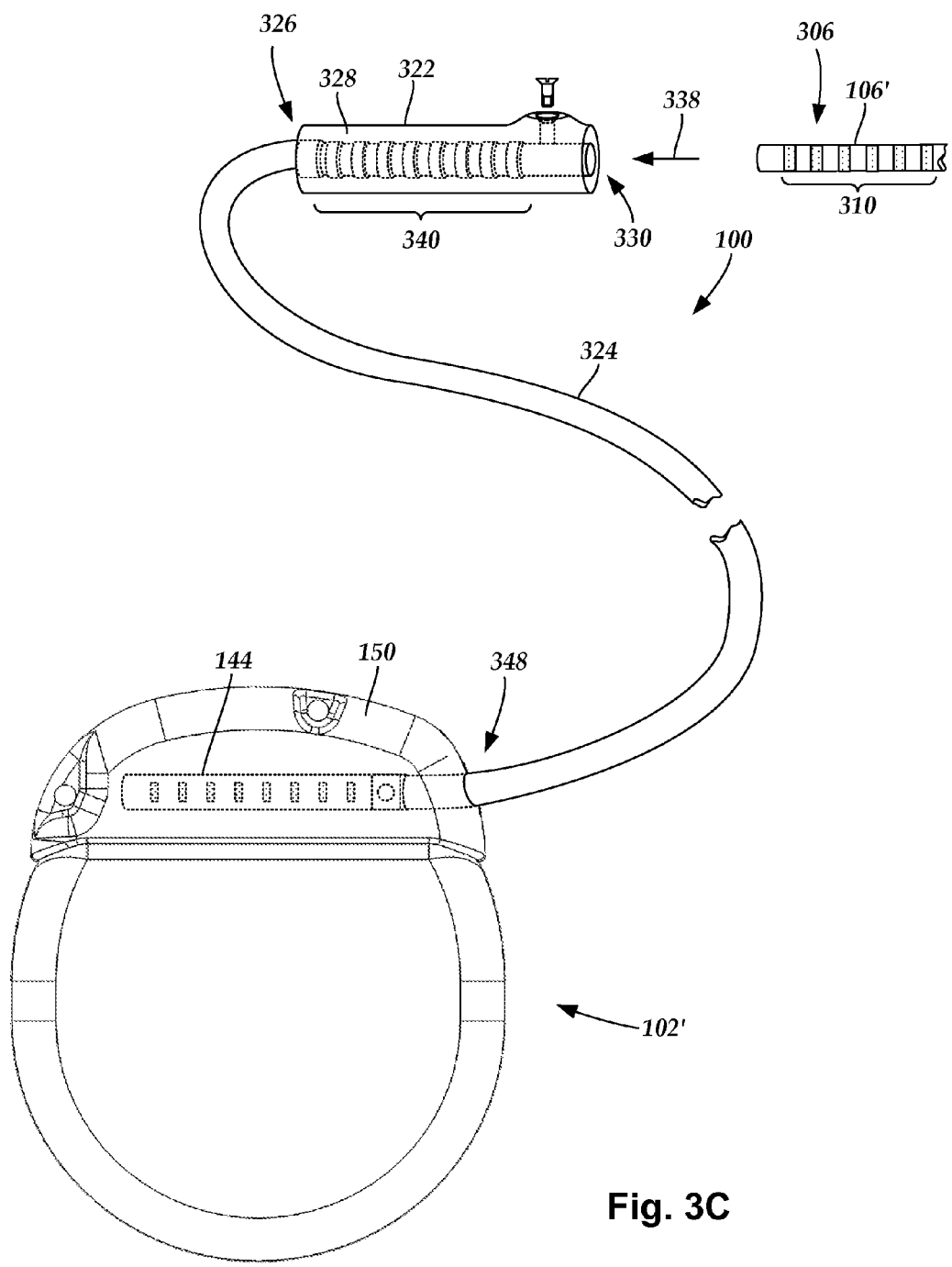
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Delivery of current to the electrodes causes charge (a product of current and pulse width) to flow through the electrodes. In some cases, in order to provide efficacious therapy to the patient, the current received by patient tissue in proximity to the electrodes needs to be within a therapeutic range. When the current is below the therapeutic range, the current may not be strong enough to provide efficacious therapy. When the current is above the therapeutic range, one or more ill effects may occur to the patient (e.g., cell death, patient discomfort, undesired paresthesia, or the like).

Delivery of charge to the electrodes results in a charge density on the electrodes. The charge density of a particular electrode is a result of a number of different factors including, for example, the strength of the current, the pulse width of the current, the effective surface area of the electrodes (e.g., the portion of the electrodes through which current flows to patient tissue), and the like. In at least some instances, a high charge density may have unwanted results. For example, a high charge density at a platinum electrode may cause undesired hydrogen bubbles to form at the electrodes. The hydrogen bubbles may be harmful to the patient. Additionally, the hydrogen bubbles may cause the electrodes themselves to degrade or corrode, thereby causing decreased or unpredictable performance of the electrical stimulation system, and potentially requiring premature explantation of the electrode lead or stimulator.

It is often desirable to reduce the size of electrodes for a variety of reasons, for example, patient comfort, ease of implantation, providing more electrodes to offer more selectivity in choice of stimulation site, and the like. As electrode size decreases, the effective surface area also decreases, which typically results in higher charge density for a given stimulation current. Additionally, as the number of stimulation channels is increased in implantable control modules, the number of electrodes disposed on the leads that couple to these devices can, likewise, be increased. The leads (e.g., paddle leads, percutaneous leads, or the like), however, are often formed to be the physical same size, despite an increase in the number of electrodes disposed on the leads. Consequently, the physical sizes of the electrodes can be reduced to accommodate the greater number of electrodes disposed on the same physical lead space. Reducing the physical size of the electrodes may increase current densities passing through the smaller electrodes. To address these issues, it may be possible to reduce the charge density of the one or more electrodes without increasing electrode size, by increasing the surface area of the one or more of the electrodes.

Many conventional electrodes have outer surfaces that are relatively flat and featureless. As described herein, enhanced electrodes can be made which have effective surface areas that are greater than the corresponding surface area of a similarly-sized flat-surfaced electrode. In at least some embodiments, the outer surfaces of the enhanced electrodes define one or more indentations, one or more protrusions, a combination of indentations and protrusions, or other features which increase the effective surface area of the enhanced electrodes.

It will be understood that enhanced electrodes may be used with any suitable lead of an electrical stimulation system (e.g., paddle leads, percutaneous leads, cuff leads, deep brain stimulation leads, microstimulators, or the like). Additionally, it will be understood that enhanced electrodes may be formed into any suitable shape (e.g., rectangular, oval, round, ring, segmented ring, tip, cuff, or the like) for use with different types of leads or electrical stimulation systems.

Figure 4:
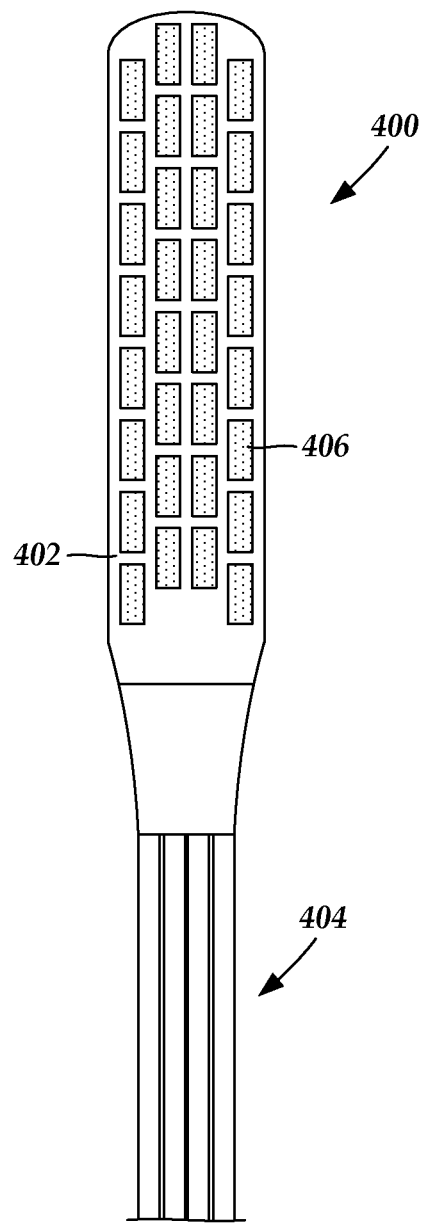
FIG. 4 is a schematic top view of one embodiment of electrodes disposed on a paddle body, according to the invention.

In at least some embodiments, enhanced electrodes may be disposed on a paddle lead. FIG. 4 is a schematic top view of one embodiment of a distal end of a paddle lead 400. The paddle lead 400 includes a paddle body 402 and one or more lead bodies 404 extending from the paddle body 402. The paddle body 402 includes a plurality of enhanced electrodes, such as enhanced electrode 406, formed on the paddle body 402. Conductors (not shown for clarity) extend from the enhanced electrodes 406 and along the one or more lead bodies 404. In at least some embodiments, each of the enhanced electrodes 406 are configured and arranged for coupling with the control module 102. In at least some embodiments, the control module 102 includes a programmable stimulation channel for each of the enhanced electrodes 406. For example, the illustrated paddle lead 400 includes 32 enhanced electrodes 406, arranged in four columns, that are configured and arranged to couple with the control module 102, which has 32 programmable stimulation channels.

The paddle lead 400 can include any number of enhanced electrodes 406 including, for example, one, two, three, four, five, six, seven, eight, nine, ten, eleven, twelve, thirteen, fourteen, fifteen, sixteen, eighteen, twenty, twenty-two, twenty-four, twenty-six, twenty-eight, thirty, thirty-two, thirty-four, thirty-six, thirty-eight, forty, forty-two, forty-four, forty-six, forty-eight, fifty, fifty-two, fifty-four, fifty-six, fifty-eight, sixty-sixty-two, sixty-four, or more enhanced electrodes 406. In FIG. 4, the paddle lead 400 is shown having thirty-two electrodes. It will be understood that other numbers of enhanced electrodes 406 may be used instead.

The enhanced electrodes 406 may be disposed on the paddle lead 400 in any suitable arrangement to provide therapy to a patient. In at least some embodiments, and as shown in FIG. 4, the enhanced electrodes 406 are arranged into columns. The enhanced electrodes 406 can be arranged into any number of columns including, for example, two, three, four, five, six, seven, eight, or more columns. In FIG. 4, the paddle lead 400 is shown having four columns. In at least some embodiments, each of the columns includes eight enhanced electrodes 406. It will be understood that other numbers of enhanced electrodes 406, either fewer or greater, may be disposed in each column. For example, at least one of the columns may include one, two, three, four, five, six, seven, eight, nine, ten, eleven, twelve, thirteen, fourteen, fifteen, sixteen, seventeen, eighteen, nineteen, twenty, or more enhanced electrodes 406. In at least some embodiments, at least one of the columns includes a different number of enhanced electrodes 406 than at least one of the other columns.

The conductors (not shown) extending along the lead bodies 404 are typically configured and arranged to couple to one or more connectors (e.g., on a control module, a lead extension, or the like) via terminals disposed on a proximal end of one or more of the lead bodies 404. In at least some embodiments, conductive wires extending from the enhanced electrodes 406 can be arranged into a plurality of distinct groupings, and each grouping disposed in a different one of the one or more lead bodies 404. In at least some embodiments, each of the one or more lead bodies 404 is configured and arranged for direct insertion into the one or more connectors.

FIGS. 5A-8B show several different embodiments of enhanced electrodes 406a-d suitable for use with the paddle lead 400. Each of the embodiments shown in FIG. 5A-8B includes a plurality of indentations defined along the outer surfaces of the enhanced electrodes. The indentations increase the effective surface area of the enhanced electrodes such that the surface area of the enhanced electrode is greater than the corresponding surface area of a similarly-sized electrode with a relatively flat surface area.

As described herein, increasing the effective surface area of the electrodes can reduce the charge density on the electrodes when a given current is provided to the electrodes. The charge density is equal to the charge provided to the electrode divided by the effective surface area of the electrode. Thus, by increasing the effective surface area of the electrode, the charge density on the actual exposed surface of the electrode can be reduced. Accordingly, by providing indentations or other surface textures along the effective surface area of the enhanced electrodes, an increased surface area may be achieved without a corresponding increase in the overall physical dimensions (e.g., length, width, diameter, or the like) of the enhanced electrodes. Additionally, increasing the effective surface area of the enhanced electrodes may also reduce the resistance to electrical current flowing through the enhanced electrodes. In at least some instances, reducing the overall physical dimensions of the electrodes can increase resistance to the delivered stimulation through the electrodes, which may be an issue with some implantable pulse generators.

In at least some embodiments, enhanced electrodes may be able to deliver higher currents to patient tissue than similarly-sized electrodes with flat outer surfaces without exceeding a charge density that may otherwise cause degradation or corrosion of the electrode or other unwanted or deleterious effects. Additionally, in at least some embodiments, enhanced electrodes may be able to maintain the same charge density as a flat-surfaced electrode, while being formed with smaller overall physical dimensions than the flat-surfaced electrode.

Enhanced electrodes may include any suitable type of indentation including, for example, grooves, dimples, cracks, fissures, notches, dents, depressions, gouges, incisions, nicks, clefts, gaps, mills, ruts, scores, cuts, trenches, scratches, channels, knurls, or the like or combinations thereof. In at least some embodiments, enhanced electrodes may include one or more projections to increase the surface area of the electrodes. Any suitable projections may be used including, for example, one or more knobs, ridges, features, domes, bulges, juts, outthrusts, spurs, shelves, protuberances, or the like or combinations thereof.

Enhanced electrodes may include any suitable number of indentations including, for example, one, two, three, four, five, six, seven, eight, nine, ten, eleven, twelve, thirteen, fourteen, fifteen, sixteen, seventeen, eighteen, nineteen, twenty, twenty-five, thirty, thirty-five, forty, forty-five, fifty, sixty, seventy, eighty, ninety, one hundred, two hundred, five hundred, or more indentations.

Indentations can be formed along the outer surface of enhanced electrodes using any suitable method of manufacture including, for example, electric discharge machining, stamping, laser machining, etching, knurling, application of one or more surface coatings onto the outer surface, roughing of the outer surface, or the like or combinations thereof.

Figure 5A:
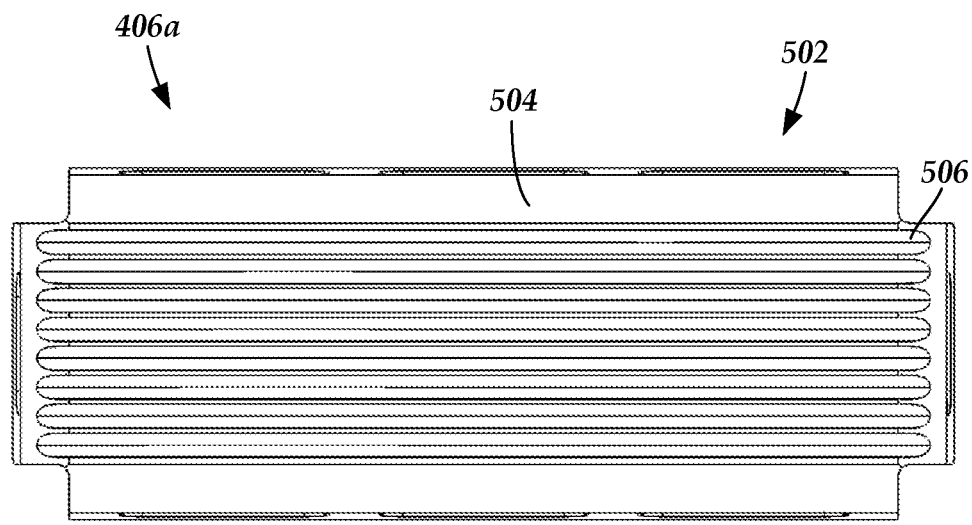
FIG. 5A is a schematic top view of one embodiment of an enhanced electrode with a plurality of longitudinally-extending grooves, the enhanced electrode suitable for use in an electrical stimulation system, according to the invention.
Figure 5B:
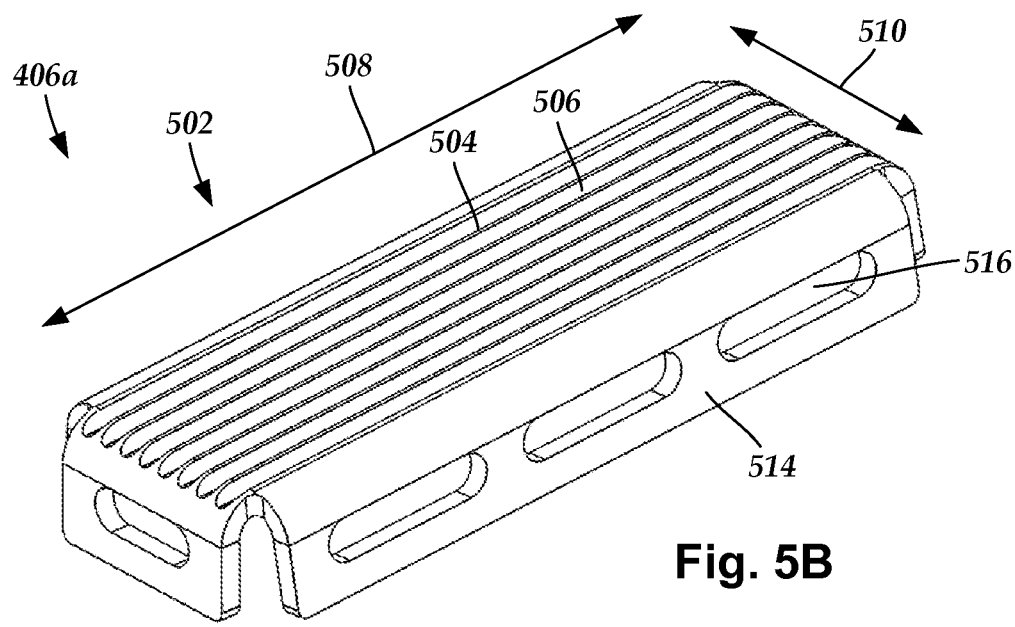
FIG. 5B is a schematic perspective view of one embodiment of the enhanced electrode of FIG. 5A, according to the invention.
Figure 5C:
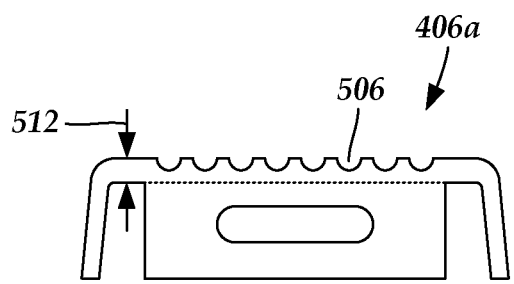
FIG. 5C is a schematic end view of one embodiment of the enhanced electrode of FIG. 5A, according to the invention.

FIG. 5A is a schematic top view of one embodiment of the enhanced electrode 406a. FIG. 5B is a schematic perspective view of one embodiment of the enhanced electrode 406a. FIG. 5C is a schematic end view of one embodiment of the enhanced electrode 406a. The enhanced electrode 406a includes a body 502 and an outer surface 504 of the body 502. The outer surface 504 defines a plurality of grooves, such as groove 506, extending at least partially along the outer surface 504. The body 502 has a length 508, a width 510, and a thickness 512.

In at least some embodiments, the enhanced electrode 406a includes one or more side walls, such as side wall 514. The one or more side walls 514 can be used to anchor the enhanced electrode 406a in the paddle body 402 by extending at least a portion of the one or more side walls 514 into the material of the paddle body 402. In at least some embodiments, at least one of the one or more side walls 514 defines one or more anchoring apertures, such as anchoring aperture 516. In at least some embodiments, during manufacturing of the lead, the material of the paddle body 402 can be flowed through the one or more anchoring apertures 516 and allowed to cure, thereby anchoring the enhanced electrode 406a in the paddle body 402.

In at least some embodiments, the grooves 506 extend longitudinally, such that the grooves 506 are parallel with the length 508 of the enhanced electrode 406a. It will be understood that the grooves 506 can extend along the outer surface 504 in any suitable direction (e.g., longitudinally, laterally, diagonally, obliquely, and the like). The grooves 506 may have any suitable length. In at least some embodiments, each of the grooves 506 has the same length. In at least some embodiments, at least one of the grooves 506 has a length that is different from at least one of the other grooves 506. In at least some embodiments, at least one of the grooves 506 extends entirely across the length 508 (or width 510) of the outer surface 504. In at least some embodiments, at least one of the grooves 506 extends no more than 90%, 80%, 70%, 60% across the length 508 (or width 510) of the outer surface 504.

The grooves 506 may have any suitable widths. In at least some embodiments, the grooves 506 have widths that are no greater than 25 μm, 50 μm, 75 μm, 100 μm, 125 μm, 150 μm, 175 μm, 200 μm, or more. In at least some embodiments, the widths of one or more of the grooves 506 are equal to the thickness 512 of the body 502 of the enhanced electrode 406a. In at least some embodiments, each of the grooves 506 has a similar width. In at least some embodiments, at least one of the grooves 506 has a width that is different from at least one of the other grooves 506.

The grooves 506 can have any suitable cross-sectional shape along one or more axes perpendicular to the outer surface 504. In at least some embodiments, the grooves 506 have a cross-sectional shape along one or more axes perpendicular to the outer surface 504 that is semi-circular. It will be understood that the grooves 506 can have other cross-sectional shapes (e.g., rounded, rectangular, triangular, or the like) along one or more axes perpendicular to the outer surface 504, as described below with reference to FIGS. 7A-7B.

The grooves 506 can have any suitable depth. In at least some embodiments, the grooves 506 have depths that are no greater than three-fourths, two-thirds, one-half, one-third, or one-fourth of the width of the grooves 506. In at least some embodiments, the depths of the grooves 506 are no greater than three-fourths, two-thirds, one-half, one-third, or one-fourth of the thickness 512 of the body 502 of the enhanced electrode 406a. In at least some embodiments, one or more of the grooves 506 extend radially inward from the outer surface 504. In at least some embodiments, one or more of the grooves 506 extend in a direction that is perpendicular to the outer surface 504. In at least some alternate embodiments, one or more of the grooves 506 extend into the enhanced electrode in a direction that is not perpendicular to the outer surface 504.

Any suitable spacing can be used between adjacent grooves 506. In at least some embodiments, adjacent grooves 506 abut one another. In at least some embodiments, the portions of the outer surface 504 disposed between adjacent grooves 506 are flat. In at least some embodiments, the entire outer surface 504 not containing one of the grooves 506 is flat.

Figure 6A:
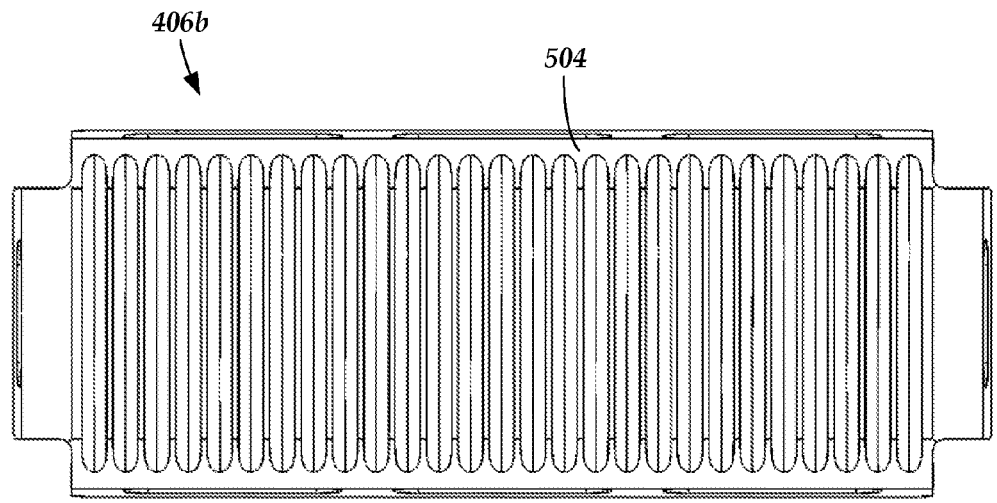
FIG. 6A is a schematic top view of one embodiment of an enhanced electrode with a plurality of laterally-extending grooves, the enhanced electrode suitable for use in an electrical stimulation system, according to the invention.
Figure 6B:
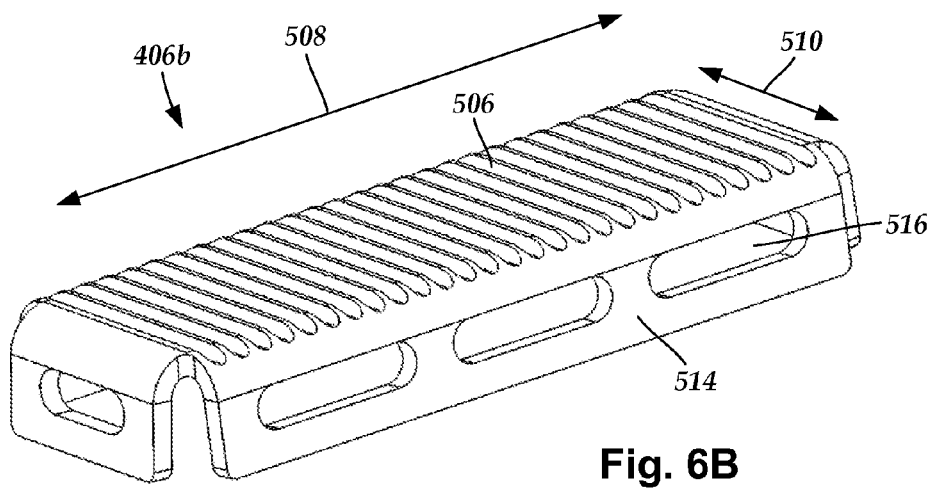
FIG. 6B is a schematic perspective view of one embodiment of the enhanced electrode of FIG. 6A, according to the invention.

In at least some embodiments, the grooves 506 extend laterally. FIG. 6A is a schematic top view of one embodiment of the enhanced electrode 406b with the grooves 506 extending laterally, such that the grooves 506 are parallel with the width 510 of the electrode. FIG. 6B is a schematic perspective view of one embodiment of the enhanced electrode 406b. In at least some embodiments, at least one of the grooves 506 extends in a direction that is different from at least one of the other grooves 506.

In at least some embodiments, the enhanced electrode 406b includes one or more side walls, such as side wall 514. The one or more side walls 514 can be used to anchor the enhanced electrode 406b in the paddle body 402 by extending at least a portion of the one or more side walls 514 into the material of the paddle body 402. In at least some embodiments, at least one of the one or more side walls 514 defines one or more anchoring apertures, such as anchoring aperture 516. In at least some embodiments, during manufacturing of the lead, the material of the paddle body 402 can be flowed through the one or more anchoring apertures 516 and allowed to cure, thereby anchoring the enhanced electrode 406b in the paddle body 402.

In FIGS. 5A-6B the grooves 506 are shown extending linearly (i.e., in straight lines). It will be understood that, in at least some embodiments, the grooves 506 can extend non-linearly (e.g., curved, wavy, swirled, zigzagged, spiraled, looped, FIG. 8, C-shaped, or the like) such that the grooves 506 do not form a straight line. In at least some embodiments, all of the grooves 506 extend non-linearly. In at least some embodiments, at least one of the grooves 506 extends linearly and at least one of the grooves 506 extends non-linearly.

Figure 7A:
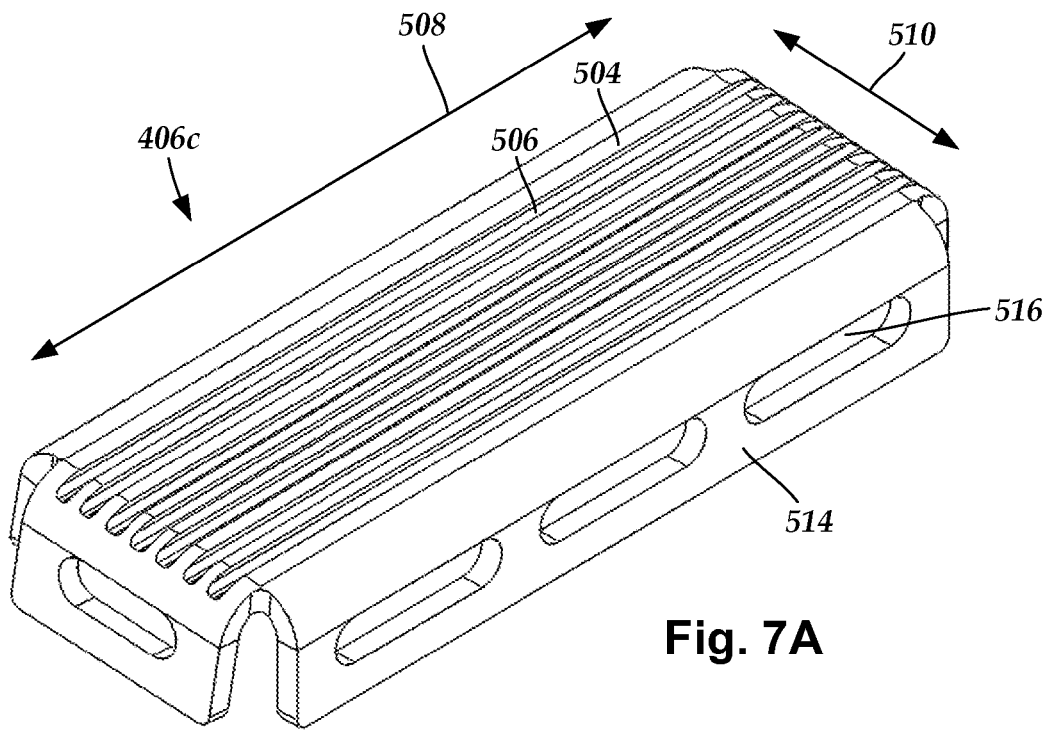
FIG. 7A is a schematic top view of one embodiment of an enhanced electrode with a plurality of longitudinally-extending, rectangular-shaped grooves, the enhanced electrode suitable for use in an electrical stimulation system, according to the invention.
Figure 7B:
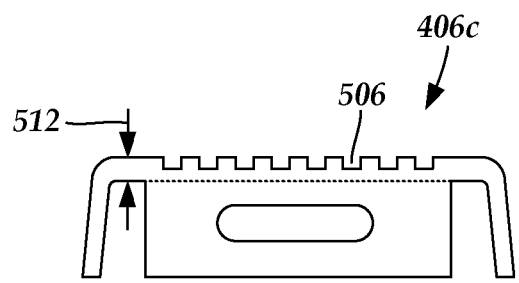
FIG. 7B is a schematic end view of one embodiment of the enhanced electrode of FIG. 7A, according to the invention.

The grooves 506 can have any suitable cross-sectional shape along one or more axes perpendicular to the outer surface 504 including, for example, semi-circular, rounded, rectangular, triangular, V-shaped, U-shaped, or the like. In FIGS. 5A-6B, the grooves 506 are shown having a semi-circular cross-sectional shape along one or more axes perpendicular to the outer surface 504 (see e.g., FIG. 5C). FIG. 7A is a schematic top view of one embodiment of the enhanced electrode 406c. FIG. 7B is a schematic end view of one embodiment of the enhanced electrode 406c. The grooves 506 defined along the outer surface 504 of the enhanced electrode 406c have rectangular-shaped cross-sectional shapes along one or more axes perpendicular to the outer surface 504.

In at least some embodiments, the enhanced electrode 406c includes one or more side walls, such as side wall 514. The one or more side walls 514 can be used to anchor the enhanced electrode 406c in the paddle body 402 by extending at least a portion of the one or more side walls 514 into the material of the paddle body 402. In at least some embodiments, at least one of the one or more side walls 514 defines one or more anchoring apertures, such as anchoring aperture 516. In at least some embodiments, during manufacturing of the lead, the material of the paddle body 402 can be flowed through the one or more anchoring apertures 516 and allowed to cure, thereby anchoring the enhanced electrode 406c in the paddle body 402.

Figure 8A:
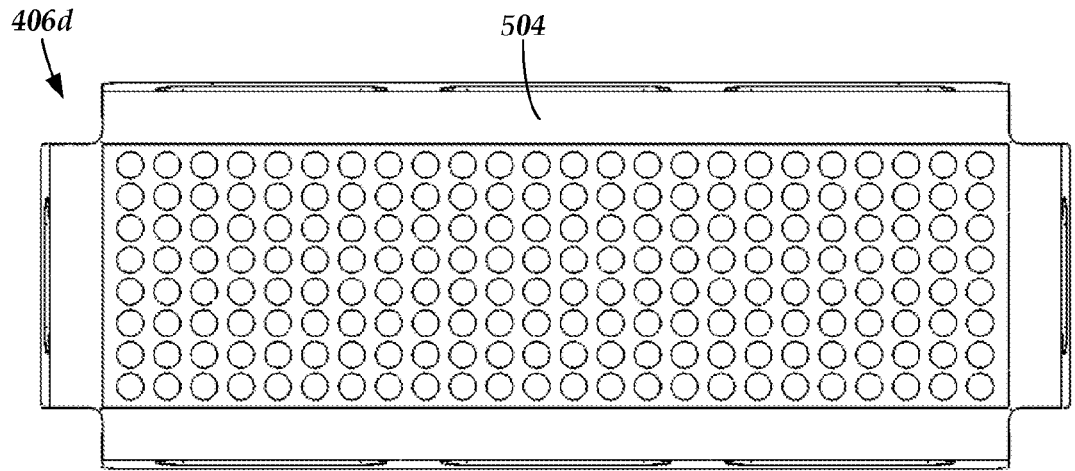
FIG. 8A is a schematic top view of one embodiment of an enhanced electrode with a plurality of dimples, the enhanced electrode suitable for use in an electrical stimulation system, according to the invention.
Figure 8B:
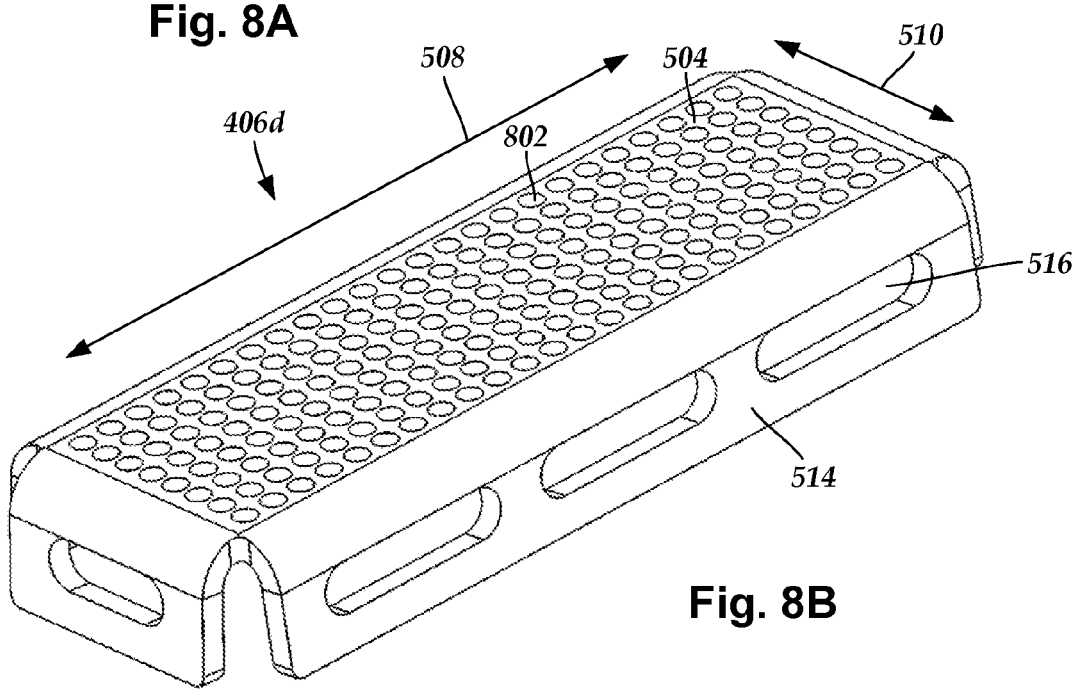
FIG. 8B is a schematic perspective view of one embodiment of the enhanced electrode of FIG. 8A, according to the invention.
Figure 8C:
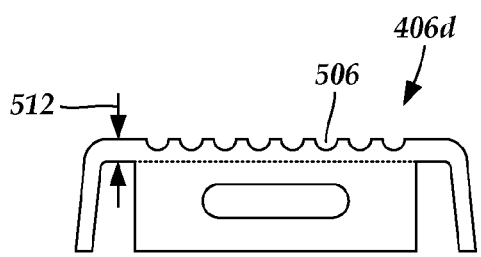
FIG. 8C is a schematic end view of one embodiment of the enhanced electrode of FIG. 8A, according to the invention.

As discussed above, any suitable indentation can be defined along the outer surface 504 of the enhanced electrode 406. In at least some embodiments, the outer surface 504 of the electrode 406 defines one or more dimples. FIG. 8A is a schematic top view of one embodiment of the enhanced electrode 406d. FIG. 8B is a schematic perspective view of one embodiment of the enhanced electrode 406d. FIG. 8C is a schematic end view of one embodiment of the enhanced electrode 406d. The enhanced electrode 406d includes dimples, such as dimple 802, defined along the outer surface 504 of the enhanced electrode 406d.

In at least some embodiments, the enhanced electrode 406d includes one or more side walls, such as side wall 514. The one or more side walls 514 can be used to anchor the enhanced electrode 406d in the paddle body 402 by extending at least a portion of the one or more side walls 514 into the material of the paddle body 402. In at least some embodiments, at least one of the one or more side walls 514 defines one or more anchoring apertures, such as anchoring aperture 516. In at least some embodiments, during manufacturing of the lead, the material of the paddle body 402 can be flowed through the one or more anchoring apertures 516 and allowed to cure, thereby anchoring the enhanced electrode 406d in the paddle body 402.

The dimples 802 can be arranged in any suitable linear or non-linear configuration (e.g., rows, columns, concentric circles, one or more patterns, randomly, or the like) along the outer surface 504 of the enhanced electrode 406d. In FIGS. 8A-8C, the dimples 802 are arranged into rows and columns. Any suitable number of dimples 802 can be disposed along the outer surface 504 of the enhanced electrode 406d. Any suitable spacing can be used between adjacent dimples 802. In at least some embodiments, the space between adjacent dimples 802 is flat. In at least some embodiments, the entire outer surface 504 not containing one of the dimples 802 is flat. The dimples 802 can have any suitable depth. In at least some embodiments, each of the dimples 802 has a depth that is no more than one half of the thickness 512 of the enhanced electrode 406d.

The dimples 802 can have any suitable shape along an axis parallel to the outer surface 504 including, for example, round, oval, triangular, rectangular, diamond, star, asterisk, cruciform, pentagonal, hexagonal, heptagonal, octagonal, nonagonal, decagonal, or the like. In at least some embodiments, the dimples 802 have a non-geometric shape along an axis parallel to the outer surface 504.

The dimples 802 can have any suitable diameter. In at least some embodiments, each of the dimples 802 has a diameter that is no greater than the thickness 512 of the enhanced electrode 406d. In at least some embodiments, each of the dimples 802 has the same diameter. In at least some alternate embodiments, at least one of the dimples 802 has a diameter that is different from the diameter of at least one of the other dimples 802. In at least some embodiments, the dimpled outer surface 504 of the enhanced electrode 406d has a surface area that is twice a surface area of a similarly-dimensioned electrode with a flat outer surface.

The dimples 802 can have any suitable cross-sectional shape along one or more axes perpendicular to the outer surface 504. The dimples 802 shown in FIG. 8A-8C are formed as hemi-spherical dimples on the outer surface 504. It will be understood that the dimples 802 can have any suitably-shaped cross-sectional shape along one or more axes perpendicular to the outer surface 504 including, for example, semi-circular, semi-elliptical, rounded, rectangular, triangular, V-shaped, U-shaped, or the like. In at least some embodiments, the dimples 802 have a surface shape on the outer surface 504 that is circular, rectangular, or triangular. In at least some embodiments, the enhanced electrode 406d includes dimples 802 each having the same cross-sectional shape along one or more axes perpendicular to the outer surface 504. In at least some alternate embodiments, at least one of the dimples 802 has a cross-sectional shape along one or more axes perpendicular to the outer surface 504 that is different from the corresponding cross-sectional shape of at least one of the other dimples 802.

In at least some embodiments, the enhanced electrode 406 includes both grooves 506 and dimples 802. In at least some embodiments, the enhanced electrode 406 includes one or more other types of indentations (e.g., grooves, dimples, cracks, fissures, notches, dents, depressions, gouges, incisions, nicks, clefts, gaps, mills, ruts, scores, cuts, trenches, scratches, channels, or the like or combinations thereof) in lieu of, or in combination with, one or more grooves 506, one or more dimples 802, or one or more grooves 506 and one or more dimples 802.

Turning to FIGS. 9A-13B, enhanced electrodes may also be used with leads other than paddle leads. As mentioned above, in at least some embodiments, enhanced electrodes can be used with percutaneous leads (e.g., spinal cord stimulation leads), deep brain stimulation leads, cuff leads, or the like. In at least some embodiments, enhanced electrodes can be formed as ring electrodes. The enhanced electrodes used in conjunction with percutaneous leads or deep brain stimulation leads have outer surfaces with increased surface areas from similarly-sized ring electrodes with non-indented or non-projecting surfaces.

In at least some embodiments, the enhanced electrodes used in conjunction with percutaneous leads or deep brain stimulation leads define a plurality of indentations. In at least some embodiments, the enhanced electrodes used in conjunction with percutaneous leads or deep brain stimulation leads include a plurality or projections. In at least some embodiments, the enhanced electrodes used in conjunction with percutaneous leads or deep brain stimulation leads define a plurality or indentations and a plurality of projections.

Figure 9A:
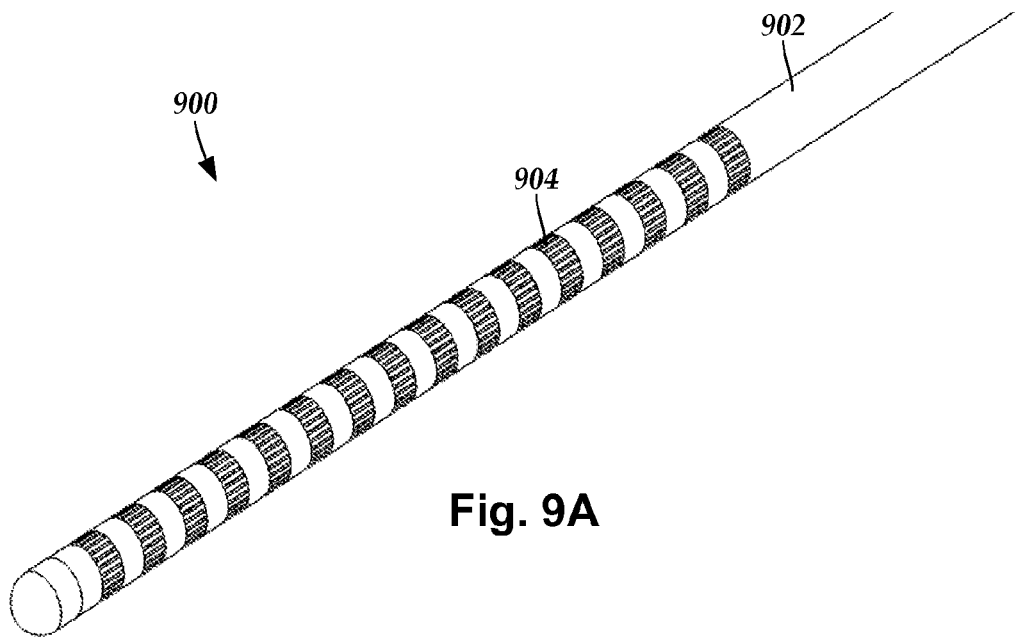
FIG. 9A is a schematic perspective view of one embodiment of a distal end of a percutaneous lead that includes enhanced electrodes with linearly-extending grooves, according to the invention.

In at least some embodiments, the enhanced electrodes are formed as ring electrodes. FIG. 9A is a schematic perspective view of one embodiment of a distal end of a percutaneous lead 900. The lead 900 includes a lead body 902 and ring-shaped enhanced electrodes, such as enhanced electrode 904, disposed axially along the lead body 902. Any suitable number of enhanced electrodes 904 may be disposed on the lead 900. In at least some embodiments, the lead 900 includes at least eight, or at least sixteen enhanced electrodes 904. In at least some embodiments, the lead 900 include no more than sixteen, or no more than eight enhanced electrodes 904.

Figure 9B:
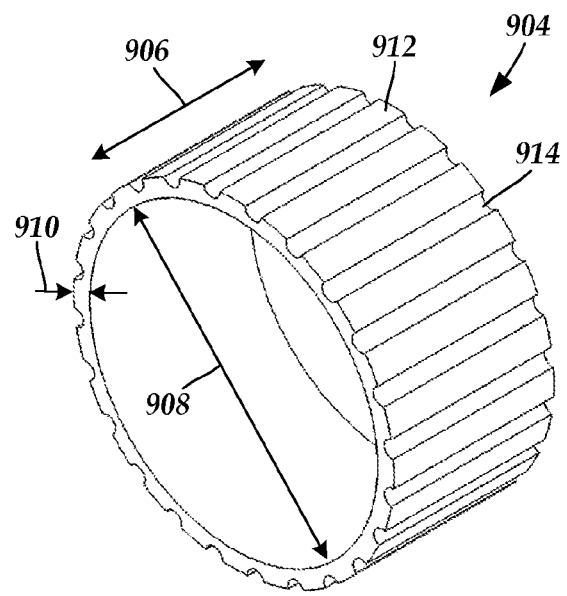
FIG. 9B is a schematic perspective view of one embodiment of one of the enhanced electrodes of the lead of FIG. 9A, according to the invention.

The enhanced electrode 904 includes a plurality of indentations. In at least some embodiments, the indentations include grooves. FIG. 9B is a schematic perspective view of one embodiment of one of the enhanced electrodes 904. The enhanced electrode 904 includes a width 906, a diameter 908, a thickness 910, and an outer surface 912. The enhanced electrode 904 defines grooves 914 defined along the outer surface 912. The sizes, shapes, depths, orientations, and arrangements of the grooves 914 can be varied, as discussed above with regards to the electrode 406. It may be an advantage to form the grooves 914 such that the grooves 914 extend in a direction that is parallel with the width 906 of the enhanced electrode 904, as shown in FIGS. 9A-9B. Forming the grooves 914 to extend in a direction that is parallel with the width 906 of the enhanced electrode 904 may promote tissue adhesion.

Figure 10A:
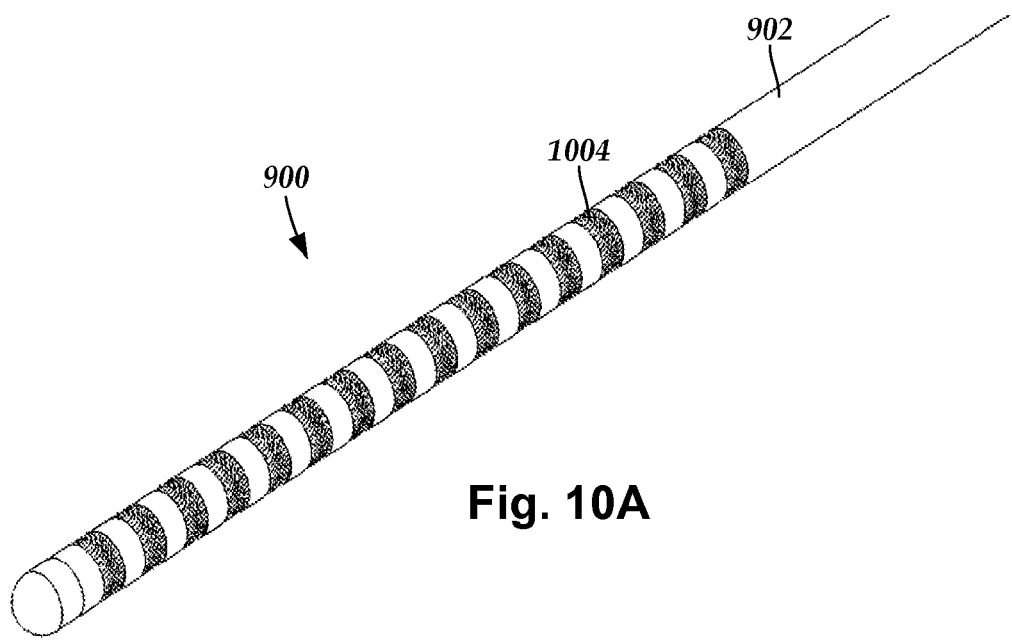
FIG. 10A is a schematic perspective view of one embodiment of a distal end of a percutaneous lead that includes enhanced electrodes with non-linearly-extending grooves, according to the invention.

As discussed above with reference to FIGS. 6A-6B, the grooves can extend along the enhanced electrode linearly or non-linearly (e.g., curved, wavy, swirled, zigzagged, spiraled, looped, FIG. 8, C-shaped, or the like) such that the grooves 506 do not form a straight line. FIG. 10A is a schematic perspective view of another embodiment of the distal end of the percutaneous lead 900. The lead 900 includes ring-shaped enhanced electrodes, such as enhanced electrode 1004, disposed axially along the lead body 902.

Figure 10B:
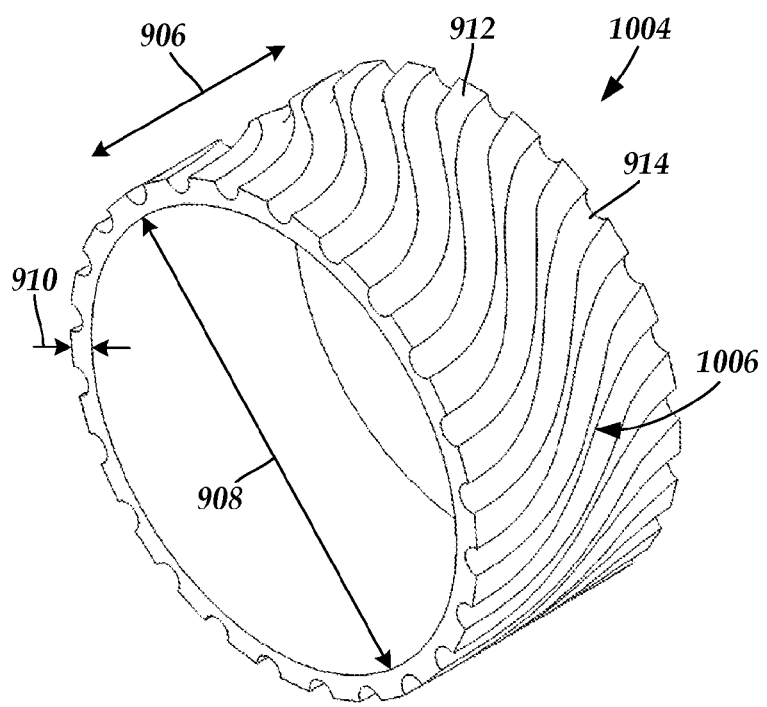
FIG. 10B is a schematic perspective view of one embodiment of one of the enhanced electrodes of the lead of FIG. 10A, according to the invention.

FIG. 10B is a schematic perspective view of one embodiment of one of the enhanced electrodes 1004. The enhanced electrode 1004 includes the width 906, the diameter 908, the thickness 910, and the outer surface 912. The enhanced electrode 1004 defines grooves 914 defined along the outer surface 912. In FIGS. 10A-10B, the grooves 914 include waves 1006 and extend non-linearly (e.g., form curved lines, form non-straight lines, or the like) along the outer surface 912 of the enhanced electrode 1004.

Figure 11A:
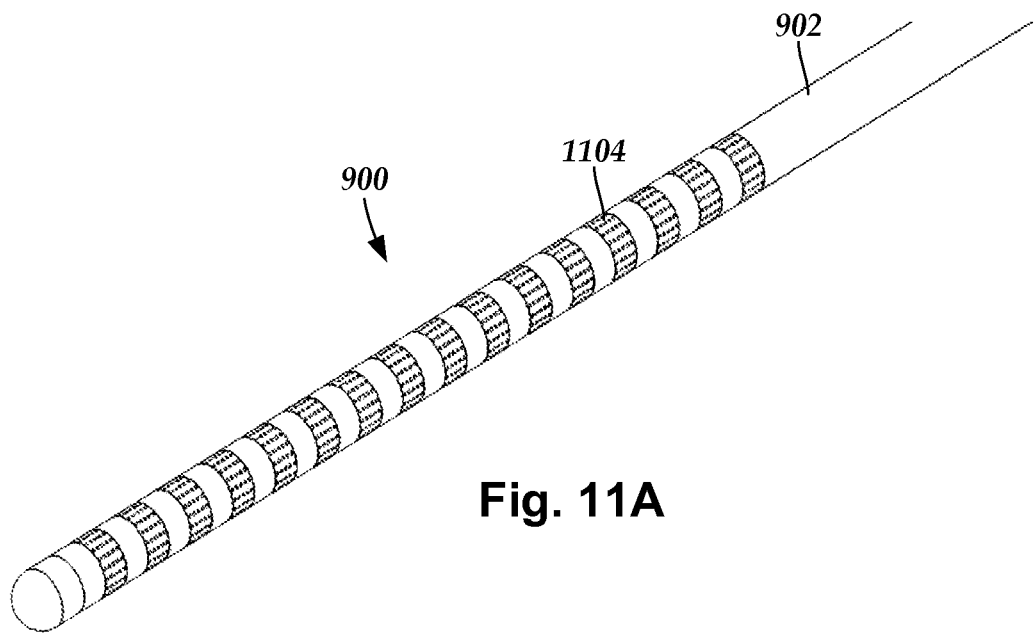
FIG. 11A is a schematic perspective view of one embodiment of a distal end of a percutaneous lead that includes enhanced electrodes with dimples, according to the invention.
Figure 11B:
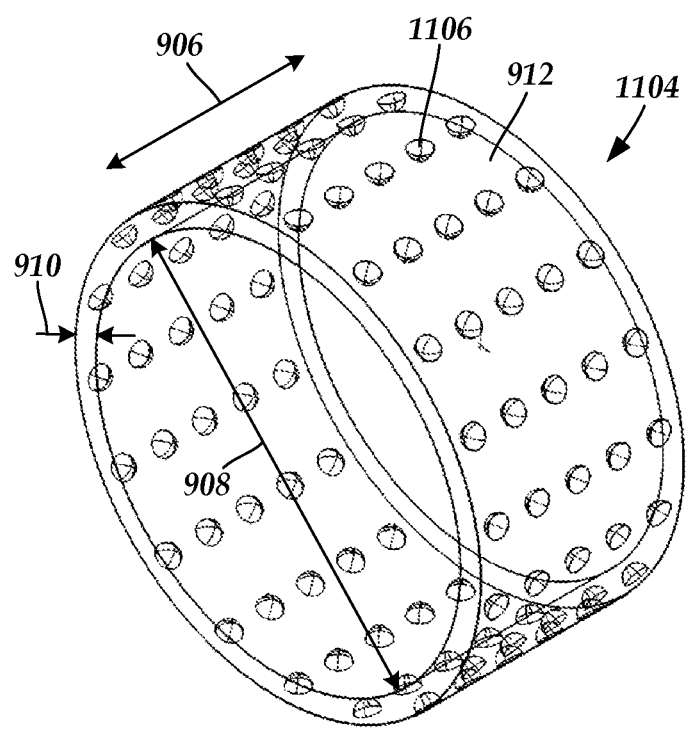
FIG. 11B is a schematic perspective view of one embodiment of one of the enhanced electrodes of the lead of FIG. 11A, according to the invention.

In at least some embodiments, the indentations include dimples. FIG. 11A is a schematic perspective view of another embodiment of the distal end of the percutaneous lead 900. The lead 900 includes ring-shaped enhanced electrodes, such as enhanced electrode 1104, disposed axially along the lead body 902. FIG. 11B is a schematic perspective view of one embodiment of one of the enhanced electrodes 1104. The enhanced electrode 1104 includes the width 906, the diameter 908, the thickness 910, and the outer surface 912. The enhanced electrode 1104 defines dimples, such as dimple 1106, defined in the outer surface 912. The sizes, shapes, depths, orientations, and arrangements of the dimples 1106 can be varied, as discussed above with regards to the electrode 406d, and with reference to FIGS. 8A-8C.

Turning now to FIGS. 12A-13B, in at least some embodiments, enhanced electrodes may be formed as segmented electrodes. In at least some embodiments, the enhanced segmented electrodes are configured and arranged such that at least two enhanced segmented electrodes are disposed circumferentially on one part of the lead body (i.e., along a transverse cross-section of the lead body). In at least some embodiments, at least three enhanced segmented electrodes are disposed on one part of the lead body of the lead body. In at least some embodiments, at least four enhanced segmented electrodes are disposed on one part of the lead body.

Segmented leads can be used with any suitable electrical stimulation systems. In at least some embodiments, segmented leads are used for deep brain stimulation. Deep brain stimulation devices and leads are described in the art. See, for instance, U.S. Pat. No. 7,809,446; U.S. Patent Application Publications Nos. 2007/0150036; 2009/0187222; 2009/0276021; 2010/0076535; and 2010/0268298; and U.S. patent application Ser. No. 12/177,823 ("Lead With Transition and Methods of Manufacture and Use"). Each of these references is incorporated herein by reference in its respective entirety.

Figure 12A:
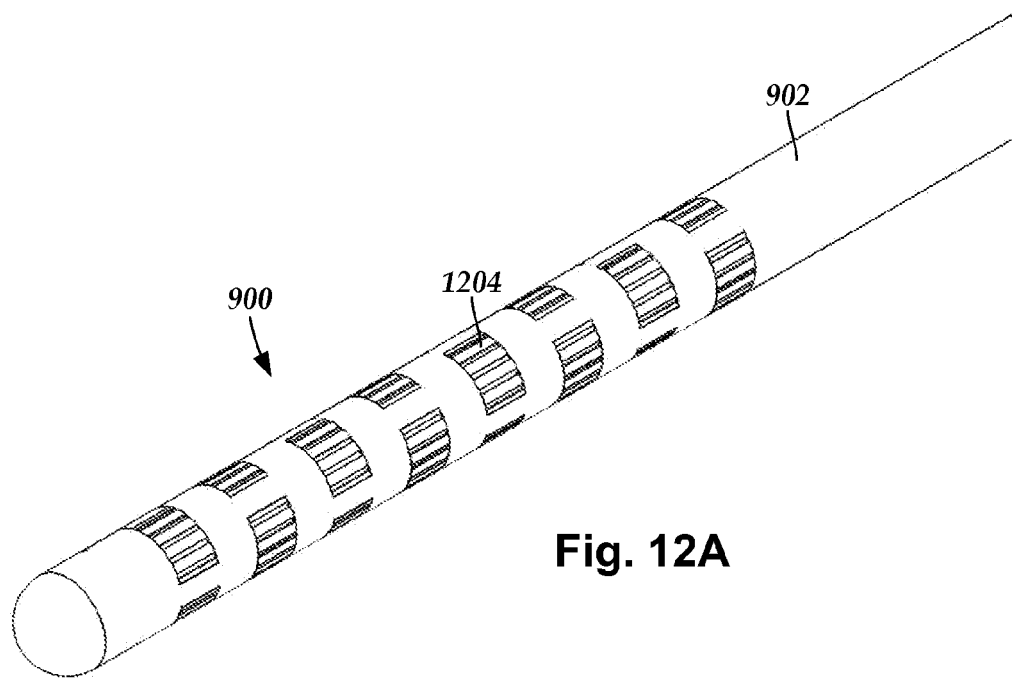
FIG. 12A is a schematic perspective view of one embodiment of a distal end of a percutaneous lead that includes enhanced segmented electrodes with grooves, according to the invention.
Figure 12B:
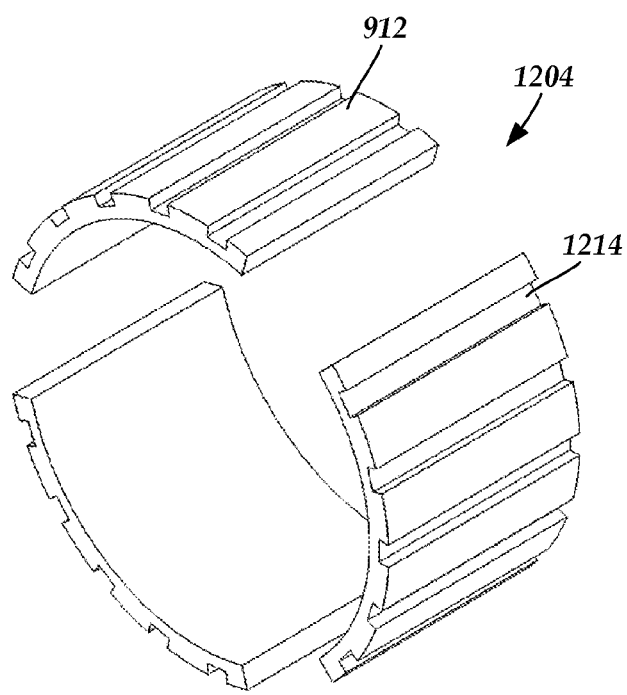
FIG. 12B is a schematic perspective view of one embodiment of one of the enhanced segmented electrodes of the lead of FIG. 12A, according to the invention.

FIG. 12A is a schematic perspective view of another embodiment of the distal end of the lead 900. The lead 900 includes enhanced segmented electrodes, such as enhanced electrode 1204, disposed axially along the lead body 902. FIG. 12B is a schematic perspective view of one embodiment of one set of the enhanced segmented electrodes 1204. The enhanced electrode 1204 defines grooves 1214 along the outer surface 912 of the enhanced electrode 1204. The sizes, shapes, depths, orientations, and arrangements of the grooves 1214 can be varied, as discussed above with regards to the enhanced electrodes 406 and 904.

Figure 13A:
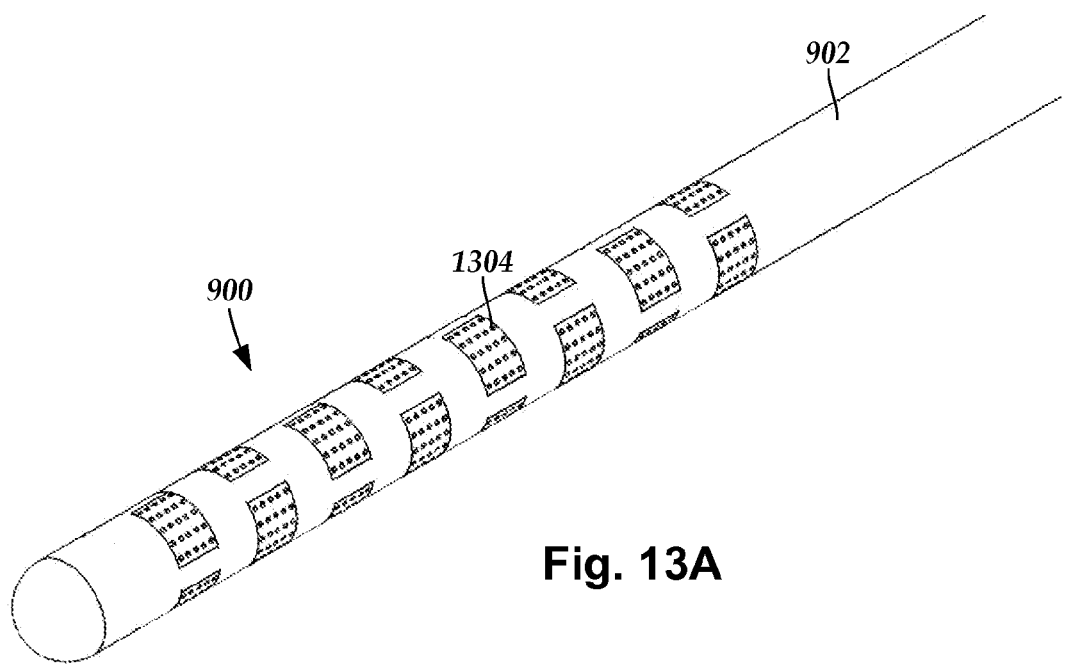
FIG. 13A is a schematic perspective view of one embodiment of a distal end of a percutaneous lead that includes enhanced segmented electrodes with dimples, according to the invention.
Figure 13B:
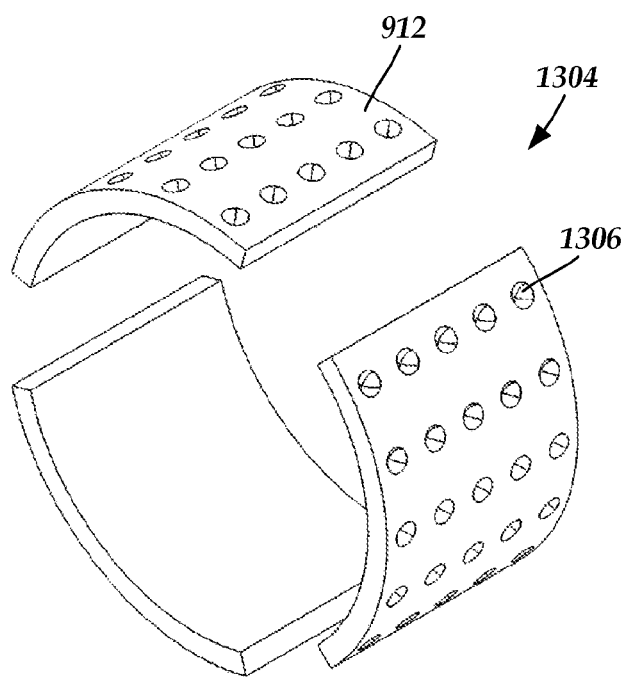
FIG. 13B is a schematic perspective view of one embodiment of one of the enhanced segmented electrodes of the lead of FIG. 13A, according to the invention.

FIG. 13A is a schematic perspective view of another embodiment of the distal end of the percutaneous lead 900. The lead 900 includes enhanced segmented electrodes, such as enhanced electrode 1304, disposed axially along the lead body 902. FIG. 13B is a schematic perspective view of one embodiment of one of the circumferential sets of enhanced segmented electrodes 1304. The enhanced segmented electrode 1304 defines dimples, such as dimple 1306, on the outer surface 912. The sizes, shapes, depths, orientations, and arrangements of the dimples 1306 can be varied, as discussed above with regards to the electrodes 406d and 1104, and with reference to FIGS. 8A-8C and 11A-11B, respectively.

Figure 14:
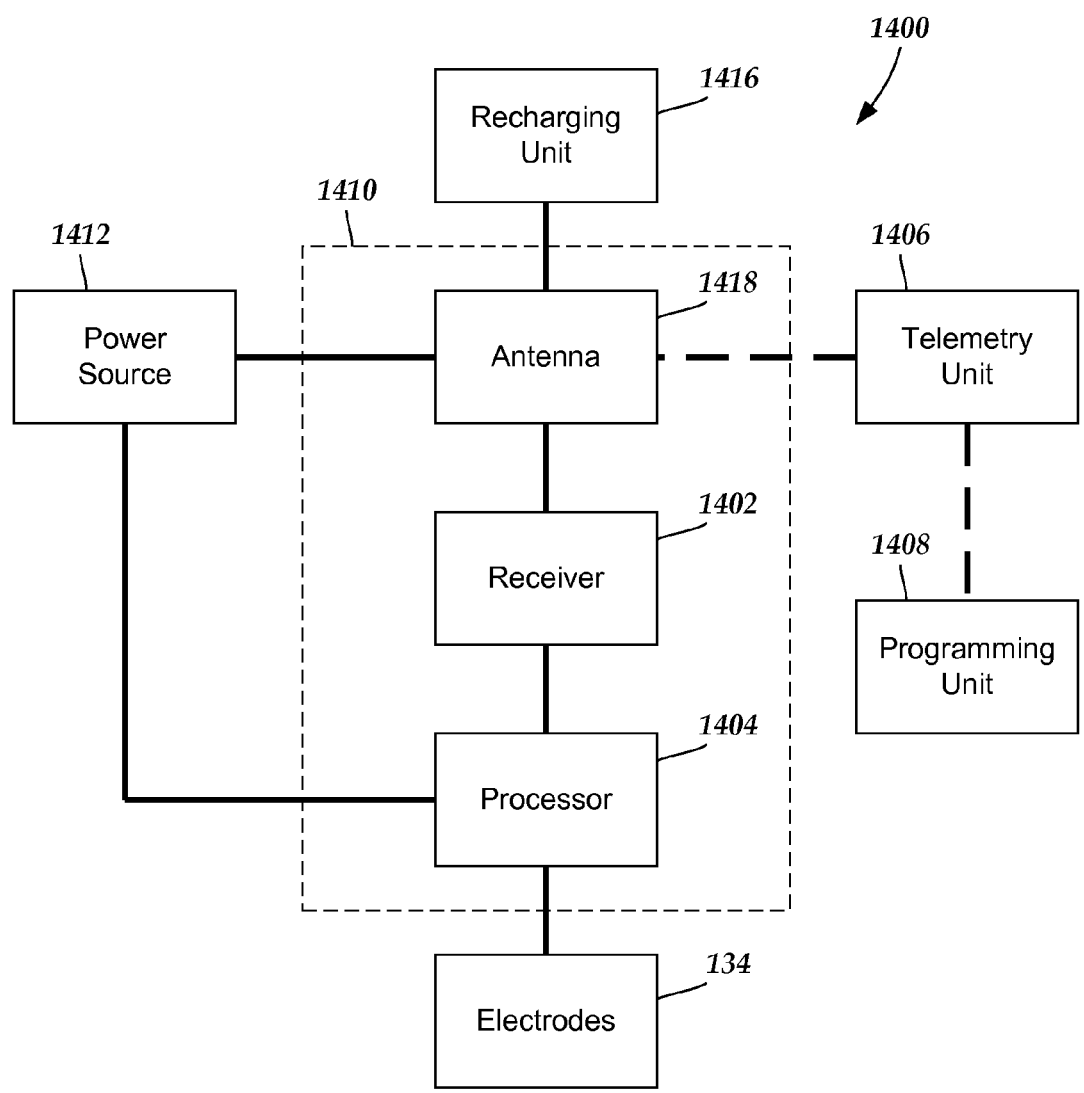
FIG. 14 is a schematic overview of one embodiment of components of a stimulation system, including an electronic subassembly disposed within a control module, according to the invention.

It will be understood that any of the indentations shown in FIGS. 9A-13B can be used in combination with one another. Moreover, any of the indentations shown in FIGS. 9A-13B can be used in combination with any other suitable indentation or FIG. 14 is a schematic overview of one embodiment of components of an electrical stimulation system 1400 including an electronic subassembly 1410 disposed within a control module. It will be understood that the electrical stimulation system can include more, fewer, or different components and can have a variety of different configurations including those configurations disclosed in the stimulator references cited herein.

Some of the components (for example, power source 1412, antenna 1418, receiver 1402, and processor 1404) of the electrical stimulation system can be positioned on one or more circuit boards or similar carriers within a sealed housing of an implantable pulse generator, if desired. Any power source 1412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1418 or a secondary antenna. The external power source can be in a device that is mounted on the skin of the user or in a unit that is provided near the user on a permanent or periodic basis.

If the power source 1412 is a rechargeable battery, the battery may be recharged using the optional antenna 1418, if desired. Power can be provided to the battery for recharging by inductively coupling the battery through the antenna to a recharging unit 1416 external to the user. Examples of such arrangements can be found in the references identified above.

In one embodiment, current is emitted by the electrodes 134 on the paddle or lead body to stimulate nerve fibers, muscle fibers, or other body tissues near the electrical stimulation system. A processor 1404 is generally included to control the timing and electrical characteristics of the electrical stimulation system. For example, the processor 1404 can, if desired, control one or more of the timing, frequency, strength, duration, and waveform of the pulses. In addition, the processor 1404 can select which electrodes can be used to provide stimulation, if desired. In some embodiments, the processor 1404 may select which electrode(s) are cathodes and which electrode(s) are anodes. In some embodiments, the processor 1404 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1408 that, for example, allows modification of pulse characteristics. In the illustrated embodiment, the processor 1404 is coupled to a receiver 1402 which, in turn, is coupled to the optional antenna 1418. This allows the processor 1404 to receive instructions from an external source to, for example, direct the pulse characteristics and the selection of electrodes, if desired.

In one embodiment, the antenna 1418 is capable of receiving signals (e.g., RF signals) from an external telemetry unit 1406 which is programmed by a programming unit 1408. The programming unit 1408 can be external to, or part of, the telemetry unit 1406. The telemetry unit 1406 can be a device that is worn on the skin of the user or can be carried by the user and can have a form similar to a pager, cellular phone, or remote control, if desired. As another alternative, the telemetry unit 1406 may not be worn or carried by the user but may only be available at a home station or at a clinician's office. The programming unit 1408 can be any unit that can provide information to the telemetry unit 1406 for transmission to the electrical stimulation system 1400. The programming unit 1408 can be part of the telemetry unit 1406 or can provide signals or information to the telemetry unit 1406 via a wireless or wired connection. One example of a suitable programming unit is a computer operated by the user or clinician to send signals to the telemetry unit 1406.

The signals sent to the processor 1404 via the antenna 1418 and receiver 1402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1400 to cease operation, to start operation, to start charging the battery, or to stop charging the battery. In other embodiments, the stimulation system does not include an antenna 1418 or receiver 1402 and the processor 1404 operates as programmed.

Optionally, the electrical stimulation system 1400 may include a transmitter (not shown) coupled to the processor 1404 and the antenna 1418 for transmitting signals back to the telemetry unit 1406 or another unit capable of receiving the signals. For example, the electrical stimulation system 1400 may transmit signals indicating whether the electrical stimulation system 1400 is operating properly or not or indicating when the battery needs to be charged or the level of charge remaining in the battery. The processor 1404 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A medical lead for providing electrical stimulation of patient tissue, the medical lead comprising:
    a lead body having a distal end portion, a proximal end portion, a circumference, and a longitudinal length;
    a plurality of electrodes disposed along the distal end portion of the lead body, each of the plurality of electrodes having a width, a length, and an outer surface, wherein at least one of the plurality of electrodes is a segmented electrode that extends around less than the entire circumference of the lead body and that is also a grooved electrode that defines a plurality of grooves along the outer surface;
    a plurality of terminals disposed along the proximal end portion of the lead body; and
    a plurality of conductive wires coupling the plurality of terminals to the plurality of electrodes.

2. The lead assembly of claim 1, wherein the at least one grooved electrode has a thickness, and each of the plurality of grooves defined along the at least one grooved electrode has a depth, and wherein the depth of each of the plurality of grooves defined along the at least one grooved electrode is no more than one-half of the thickness of the at least one grooved electrode.

3. The lead assembly of claim 1, wherein the plurality of grooves defined along the at least one grooved electrode are spaced-apart from one another such that the grooves do not abut one another.

4. The lead assembly of claim 1, wherein an entire non-grooved portion of the outer surface of the at least one grooved electrode is flat.

5. The lead assembly of claim 1, further comprising a surface coating disposed over at least a portion of the outer surface of the at least one grooved electrode.

6. The lead assembly of claim 1, wherein the plurality of grooves are defined along the outer surfaces of each of the plurality of electrodes.

7. The medical lead of claim 1, wherein the plurality of grooves extend non-linearly along the grooved electrode such that each of the plurality of grooves extends longitudinally in a curved line along the outer surface of the grooved electrode with respect to the longitudinal length of the lead body.

8. The lead assembly of claim 7, wherein the plurality of grooves extend longitudinally in curved lines along the outer surface of the grooved electrode with respect to the width of the grooved electrode.

9. The lead assembly of claim 7, wherein the plurality of grooves extend longitudinally in curved lines along the outer surface of the grooved electrode with respect to the length of the grooved electrode.

10. The medical lead of claim 1, wherein at least one groove of the plurality of grooves has one of a U-shaped cross-section or a V-shaped cross-section along a plane that is perpendicular to the outer surface and perpendicular to a length of the at least one groove of the plurality of grooves.

11. The medical lead of claim 1, wherein at least one groove of the plurality of grooves has a rectangular cross-sectional shape along a plane that is perpendicular to the outer surface and perpendicular to a length of the at least one groove of the plurality of grooves.

12. An electrical stimulating system comprising:
    the lead assembly of claim 1;
    a control module configured and arranged to electrically couple to the proximal end portion of the lead body of the lead assembly, the control module comprising
        a housing, and
        an electronic subassembly disposed in the housing; and
    a connector configured and arranged for receiving the lead body, the connector comprising
        a connector housing defining at least one port configured and arranged for receiving the proximal end portion of the lead body, and
        a plurality of connector contacts disposed in the at least one port, the plurality of connector contacts configured and arranged to couple to the plurality of terminals when the proximal end portion of the lead body is received by the port.

13. The lead assembly of claim 1, wherein the lead body is isodiametric.

14. A medical lead for providing electrical stimulation of patient tissue, the medical lead comprising:
    a lead body having a distal end portion, a proximal end portion, and a longitudinal length;
    a plurality of electrodes disposed along the distal end portion of the lead body, the plurality of electrodes each having an exterior surface and an opposing interior surface, wherein the plurality of electrodes are configured and arranged such that when the lead is implanted in a patient the exterior surfaces of each of the plurality of electrodes are exposed to patient tissue and provide a surface along which stimulation energy propagates from the lead to patient tissue, wherein at least one of the plurality of electrodes is a grooved electrode, wherein a plurality of grooves are defined along the exterior surface of the at least one grooved electrode and extend non-linearly with each of the plurality of groove extending in a curved line around less than an entire circumference of the lead, wherein the interior surface of the at least one grooved electrode is ungrooved;
    a plurality of terminals disposed along the proximal end portion of the lead body; and
    a plurality of conductive wires coupling the plurality of terminals to the plurality of electrodes.

15. The lead assembly of claim 14, further comprising a paddle body disposed along the distal end portion of the lead body, wherein the at least one grooved electrode is disposed on the paddle body.

16. The lead assembly of claim 15, wherein the at least one grooved electrode comprises at least one side wall at least partially inset into the paddle body.

17. The lead assembly of claim 16, wherein the at least one grooved electrode comprises at least one anchoring aperture defined in the at least one side wall, the at least one anchoring aperture configured and arranged to receive a portion of the paddle body.

18. The lead assembly of claim 14, wherein the at least one grooved electrode is a ring electrode.

19. The medical lead of claim 14, wherein the plurality of grooves extend longitudinally with respect to the longitudinal length of the lead body across an entire length of the at least one grooved electrode.

20. The medical lead of claim 14, wherein the interior surface of the at least one grooved electrode is flat.

* * * * *